United States Patent [19]

McCabe et al.

[11] Patent Number: 5,102,765

[45] Date of Patent: Apr. 7, 1992

[54] TONER COMPOSITIONS CONTAINING 2-IMIDAZOLINES, IMIDAZOLES OR BENZIMIDAZOLES AS CHARGE CONTROL AGENTS

[75] Inventors: John M. McCabe, Pittsford; John C. Wilson, Rochester, both of N.Y.

[73] Assignee: Eastman Kodak Company, Rochester, N.Y.

[21] Appl. No.: 563,004

[22] Filed: Aug. 6, 1990

[51] Int. Cl.$^5$ .............................................. G03G 9/097
[52] U.S. Cl. ...................................................... 430/110
[58] Field of Search ......................................... 430/110

[56] References Cited

U.S. PATENT DOCUMENTS

| | | | |
|---|---|---|---|
| 3,669,886 | 6/1972 | Kosel | 430/106 X |
| 3,959,404 | 5/1976 | Labana | 430/109 X |
| 4,258,116 | 3/1981 | Takasu | 430/110 X |
| 4,291,111 | 9/1989 | Lu | |

FOREIGN PATENT DOCUMENTS

| | | |
|---|---|---|
| 0340928 | 4/1989 | European Pat. Off. |
| 56-146167 | 4/1980 | Japan |
| 59-185349 | 4/1983 | Japan |
| 59-187350 | 4/1983 | Japan |
| 61-259265 | 5/1985 | Japan |
| 61-294461 | 6/1985 | Japan |
| 62-242960 | 4/1986 | Japan |

*Primary Examiner*—Roland Martin
*Attorney, Agent, or Firm*—Dressler, Goldsmith, Shore, Sutker & Milnamow

[57] ABSTRACT

A toner composition comprising a binder and a 2-imidazoline is provided.

1 Claim, No Drawings

TONER COMPOSITIONS CONTAINING 2-IMIDAZOLINES, IMIDAZOLES OR BENZIMIDAZOLES AS CHARGE CONTROL AGENTS

FIELD OF THE INVENTION

This invention is in the field of charge control agents for toner compositions.

BACKGROUND OF THE INVENTION

In the electrophotography art, there is a need for charge control agents that do not increase the temperature required to adequately fuse the toner powders containing the same. Lower fusing temperatures are desirable because they permit copiers to operate at lower temperatures which increases the useful life of machine components in the copier such as the photoconductor films, electronic components, fuser roll and the like. A reduction in fusing temperature also reduces power consumption, copier warmup time, and problems with paper receivers and permits higher speed fusing.

One approach that has been tried to achieve these results is to utilize conventional charge control agents such as quaternary ammonium compounds, amines, phosphoniums and the like. However, these charge control agents undesirably increase the temperature required to adequately fuse the toner powder and/or can result in the equivalent fusing quality not being attained at any temperature. Furthermore, many of these charge control agents are very expensive.

For example, the conventional charge control agent N-octadecyl-N,N-dimethylbenzylammonium m-nitrobenzenesulfonate can increase the fusing temperature of a toner powder by 25° to 50° F.

So far as is now known, the problem of controlling the charge in toner powders while maintaining a low fusing temperature and good fusing quality has not been solved.

SUMMARY OF THE INVENTION

This invention relates to toner compositions containing 2-imidazolines, imidazoles or benzimidazoles as charge control agents.

The toner compositions of the present invention permit the use of lower fusing temperatures and show no adverse effect upon fusing performance.

Various other features, advantages, aims, purposes, embodiments and the like of this invention will be apparent to those skilled in the art from the present specification and appended claims.

DETAILED DESCRIPTION OF THE PREFERRED EMBODIMENTS

The term "glass transition temperature" or "$T_g$" as used herein means the temperature at which a polymer changes from a glassy state to a rubbery state. This temperature ($T_g$) can be measured by differential thermal analysis as disclosed in "Techniques and Methods of Polymer Evaluation," Vol. 1, Marcel Dekker, Inc., N.Y. 1966.

The term "reactable carboxyl groups per molecule" as used herein in relation to a polymer means that the polymer contains pendant and/or terminal carboxyl groups in an acid form that are reactable with a low molecular weight epoxy novolac resin.

The term "reactable hydroxyl groups per molecule" as used herein in relation to a polymer means that the polymer contains pendant and/or terminal hydroxyl (—OH) groups that are reactable with an acidic moiety, such as pyromellitic dianhydride.

The term "charge control agent" as used herein means a substance which alters the triboelectric charging capacity of toner particles.

The term "onset of fusing temperature" as used herein in relation to a toner powder means the lowest temperature at which a high density solid area patch developed with this toner, after being run through a fuser nip, folded upward with loose toner brushed off the fold, exhibits $<100\mu$ crack width (i.e., good adhesion to paper) measured on a Canon PC type fusing breadboard consisting of an non-oiled hard Teflon fusing roll engaged onto a compliant rubber backup roll at a constant speed and pressure.

The term "fusing latitude" as used herein means the fusing range at constant speed and pressure from the onset of fusing temperature to the hot offset temperature (i.e., lowest temperature at which some of the fused image "offsets" onto the fusing roll surface as observed by running a blank chase sheet through the fuser immediately after the toned image). The hot offset condition occurs when the interfacial bond strength of the molten toner to the fusing roll exceeds the hot melt cohesive strength of the toner.

The term "low molecular weight" as used herein means a number average molecular weight under about 2,500.

The term "keep" or "keeping" as used herein in relation to a toner powder means the storage stability of the toner powder (i.e., its ability to retain its original particle size distribution when stored in a cartridge at a specified range of temperature and RH conditions). An accelerated keep best measures the ability of the toner to retain its fine powder flow characteristics. A small amount of toner is added to a cylindrical glass vial. A cylindrical weight is placed over the packed toner layer (to simulate the toner at the bottom of a cartridge) and the vial is placed in an oven for a set period of time at a set temperature. Tone keep is controlled by the glass transition temperature or softening point of the toner. The keep is subjectively evaluated by removing the toner from the vial after the incubation period and determining its powder characteristics by applying some pressure to the packed powder. If it retains its original powder form without applying any pressure or with slight pressure it rates good to excellent. A fair keep indicates that some pressure is required to break up the clump. Poor and fused keep ratings indicate partial or total sintering of the packed powder.

The charge control agents can be 2-imidazolines, imidazoles or benzimidazoles.

2-Imidazolines may be represented by the following general structure:

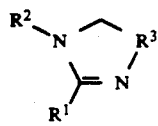

where $R^1$ is aromatic and substituted aromatic, such as phenyl, 2-chlorophenyl, 2-hydroxyphenyl, 4-chlorophenyl, 4-methylphenyl, and the like, alkyl such as undecyl and the like, aralkyl, such as benzyl and the like, or hydrogen;

$R^2$ is hydrogen or alkyl, such as methyl and the like;

$R^1$ together with $R^2$ may be alkylene, such as 1,3-propylene, 1,5-pentylene, and the like; and $R^3$ is alkylene, such as methylene, 1,2-ethylene, isopropylidene and the like.

Representative 2-imidazolines include: 2-phenyl-2-imidazoline;
2-(2-hydroxyphenyl)-2-imidazoline;
2-(2-chlorophenyl)-2-imidazoline;
2-(4-chlorophenyl)-2-imidazoline;
2-(4-methylphenyl)-2-imidazoline;
2-n-undecyl-2-imidazoline;
2-benzyl-2-imidazoline;
4,4-dimethyl-2-imidazoline;
1,5-diazabicyclo[4.3.0]non-5-ene; and
2.8-diazobicyclo[5.4.0]undec-7-ene.

Imidazoles and benzimidazoles may be represented by the following general structure:

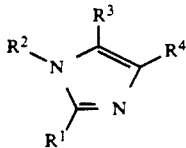

where
$R^1$ is aromatic, such as phenyl;
$R^2$ is alkyl, such as methyl;
$R^3$ is hydrogen;
$R^4$ is hydrogen;
$R^1$ together with $R^2$ may form a six-membered ring system such as when $R^1+R^2$ is $-CH=CH-CH=CH-$; and
$R^3$ together with $R^4$ may form a six-membered ring system such as when $R^3+R^4$ is $-CH=CH-CH=CH-$.

Representative imidazole and benzimidazole compounds include:

1-methyl-2-phenylbenzimidazole and imidazo [1,2-a]pyridine.

The charge control agent can be incorporated into a conventional toner composition by admixing the charge control agent with the components of the toner composition prior to the reaction of the components. The charge control agent can also function as a catalyst for the reaction of the components of the toner composition.

Representative toner compositions can include polyester or styrene-butyl acrylate-divinyl benzene binders.

In general, toner particles of this invention can fall in the size range of about 0.01 to about 100 microns, preferably about 1 to about 30 microns in average diameter.

In a particulate toner composition, the polymer binder is the major component of this invention. It comprises more than about 50 weight percent of the total toner particle composition weight, and preferably comprises about 75 to about 98 weight percent thereof. Colorants and the charge control agents of the present invention usually constitute the balance of the composition.

The colorant can be selected from among a wide variety or range of dyes and/or pigments. Useful colorants (including black) are described in many patents. See, for example, U.S. Pat. Nos. 4,140,644; 4,416,965; 4,414,152; and 2,229,513. The concentration of colorant in a toner composition can vary over a wide range; for example, such can be in the range of about 0.5 to about 20 weight percent, with a range of about 1 to about 6 weight percent being presently preferred, on a total composition basis.

Dry toner compositions of this invention can optionally incorporate a small quantity of low surface energy material in combination with toner particles comprised of the polyester polymer, such as described in U.S. Pat. No. 4,517,272. Presently preferred such materials include silicone oils and poly dimethyl siloxane copolymers. Examples thereof include silicone glycol copolymers, alkylaryl silicones, chlorophenylmethyl silicones, dimethyl silicone, and the like, such as are available commercially from the Dow Corning Company. Other such additives include polyvinylidene fluorides, polymonochlorotrifluoroethylenes, hexafluoropropylenevinylidene fluoride copolymers, perfluoroalkyl polyethers (such as are available commercially from the duPont Company and Montecatini-Edison), fluoroalkyl esters, block copolymers of dimethyl siloxane with various materials, such as bisphenol A, tetramethylspirobi(indan)diol, and the like. When employed, the amount of such an additive is in the range of about 0.5 to about 10 weight percent based on total weight of a toner composition.

Representative of the polyester toner compositions is the reaction product of a linear polyester resin, a polyfunctional epoxy novolac resin and a catalyst.

The polyester has an acid content of about 0.1 to about 0.7 meq/g, preferably from about 0.18 to about 0.3 meq/g, of acid functionality. The number average molecular weight is in the range of about 1,000 to about 4,000, preferably from about 1,500 to about 3,000. The weight average molecular weight is in the range of about 2,000 to about 15,000, preferably from about 3,000 to about 10,000. The polyester has a glass transition temperature ($T_g$) in the range of about 50° to about 85° C., preferably from about 60° to about 75° C.

As those skilled in the art will appreciate, the polyester can have many structures depending upon such variables as the monomers used for polycondensation and the condensation conditions employed. For example, the presence of a suitable molar excess of polyhydroxylated compound can be used to regulate the molecular weight of the polyester. All or a chosen portion of the hydroxyl groups can then be reacted (carboxylated) with a polycarboxylic acid anhydride to achieve a quantity of reactable carboxyl groups per molecule. Suitable acid anhydrides are preferably aromatic and preferably contain at least two carboxyl groups per molecule when in the hydrated (or acid) form. Examples of suitable anhydrides include pyromellitic dianhydride, trimellitic anhydride, phthalic anhydride, 3,3',4,4'-benzophenonetetracarboxylic dianhydride, glutaric anhydride, succinic anhydride, maleic anhydride, and the like. The carboxylation reaction of a polyester with such an acid anhydride is conveniently carried out at elevated temperature under liquid phase conditions.

Tri or tetra functional carboxylic acids can also be employed for condensation with diols using conditions which result in polyesters that contain a desired quantity of reactable carboxyl groups per molecule.

One presently preferred class of amorphous polyesters comprises:
about 50 to about 99 mole percent terephthalic acid;

about 0 to 49 mole percent additional diacid(s);

about 1 to about 15 mole percent trimellitic anhydride;

about 50 to about 100 mole percent neopentyl glycol; and 0 to about 50 mole percent 1,4-cyclohexanedimethanol.

It should be noted that mole percents for the polyacid components are based upon total polyacid components and glycol mole percents are based upon total glycol components.

Representative commercially available polyester resins are Cargill 3000 polyester resin and Cargill 3018 polyester resin, both from Cargill, Carpentersville, IL.

The low molecular weight epoxy novolac resin has about 2 to about 6 epoxide groups per molecule.

The term "epoxy novolac resin" as used herein means an epoxy resin made by the reaction of epichlorohydrin with a novolac resin. An epoxy novolac resin has the pendant repeating epoxide structure:

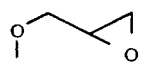

A novolac resin is a condensate of a phenol compound with formaldehyde in the presence of acid catalysts. The phenol compound can be phenol itself, or such compounds as the cresols, xylenols, resorcinol, naphthols, and the like. Epoxy novolac resins used in the practice of this invention have epoxy functionalities which are typically in the range of about 2.5 to about 6.

One presently preferred class of epoxy novolac resins comprises epoxy cresol novolac resins having a molecular weight in the range of about 500 to about 1,300. These resins are prepared by the condensation of cresol and formaldehyde followed by reaction with epichlorohydrin to produce a polymer having an epoxy functionality in the range of about 2.5 to about 6.

An example of a presently particularly preferred epoxy cresol novolac resin is characterized by the structure:

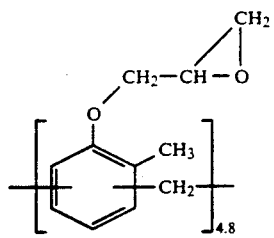

This epoxy resin is obtainable from Ciba-Geigy Corp. under the trade designation "ECN 1273" and has an epoxy functionality of about 4.8.

Alternatively, one may utilize a copolymer of styrene and butyl acrylate, crosslinked with divinyl benzene by a suspension or emulsion polymerization process. An initiator and, optionally, a chain transfer agent is used in its synthesis. The ratio of styrene to butyl acrylate is in the range of 90/10 to 60/40 and the divinyl benzene is used at a level of 0.1 to 1.0 wt. %.

The components, including the charge control agent, of the toner compositions of the present invention can be mixed prior to melt blending to achieve a uniform product.

The mixture is melt blended on heated compounding rolls or by passage through an extruder, or the like. Melt blending is accomplished at a temperature in the range of about 150° to about 240° C., and preferably in the range of about 180° to about 220° C.

Melt blending times (that is, the exposure period for melt blending temperatures) are sufficient to allow achievement of uniformity or for the reaction to be complete. Typically they are in the range of about 10 to about 20 minutes if a roll mill is utilized and about 1 to about 2 minutes if an extruder is utilized.

Grinding of the toner composition can be carried out by any convenient procedure. For example, the solid mixture can be crushed and ground to a desired particle size using, for instance, a fluid energy or jet mill, such as is described in U.S. Pat. No. 4,089,472. One or more conventional particle classification steps can be used to achieve a toner particle composition having a desired particle size and size distribution.

The weight ratio of charge control agent to toner composition is preferably in the range of about 1:1000 to about 1:25, more preferably in the range of about 1:200 to about 1:50.

The following Examples are presented by way of representation, and not limitation, of the preferred embodiments of the present invention.

EXAMPLE 1

Preparation Of 2-Imidazolines 2-(2-Chlorophenyl)-2-imidazoline was prepared by the method of Isagulyants, et al., Khimiya Geterotsiklicheskikh Soedinenii, No. 3, pp. 383–5, March, 1972:

Methyl o-chlorobenzoate (85.3 g, 0.50 mol) was added to a mixture of 150.25 g (2.50 mol) of ethylenediamine and 25.59 g of DOWEX 50W-X8, H+ form, 20–50 mesh cation exchange resin over approximately 5 mins. The mixture was then heated in a 115° C. bath for 5 hrs., cooled and filtered. After washing the ion-exchange resin with methanol, the filtrate was concentrated on a steam bath with water aspirator vacuum and then heated in a 220° C. bath for 1.5 hr with vacuum to remove water. The residue was dissolved in methylene chloride, filtered, and concentrated. The residue was distilled (bp=145°–190° C./1.7–2.0 mm). The crystalline distillate was recrystallized from acetonitrile to give 17.6 g of product; mp=76°–79° C.

Anal. Calcd. for $C_9H_9ClN_2$: C, 59.8; H, 5.0; Cl, 19.6; N, 15.5;

Found: C, 59.4; H, 5.1; Cl, 20.5; N, 15.3;

The structure was confirmed by NMR and MS.

Other 2-imidazolines were prepared in a similar manner.

EXAMPLE 2

Toner Powder Containing 2-Phenyl-2-Imidazoline

A toner powder was prepared by mixing 0.45 of the charge control agent 2-phenyl-2-imidazoline, 60.0 g of Cargill 3018, a polyester resin commercially available from Cargill, Carpentersville, Ill., 1.90 g of ECN 1273, an epoxy resin commercially available from Ciba-Geigy, and 3.67 g Regal 300, carbon black commercially available from Cabot and Company, on an 8″ roll mill for 20 minutes at a temperature of 100° C. The mixture was then introduced into the bowl of a Brabender Plasticorder mixer and reacted for 10 minutes at a temperature of 200° C. using a blade rotational speed of 90 revolutions per minute (rpm). The resultant toner composition was air pulverized using a Trost TX air pulverizer mill at 1.0 g/minute at an air pressure of 70 pounds per square inch (psi) to reduce the composition to a toner powder.

The charge/mass measurement was 37.9 μcoul/g and the fusing temperature was 335° F. which is very good.

EXAMPLE 3

Styrene Comparative Toner Powder

A conventional toner composition was prepared by emulsion polymerizing styrene and butylacrylate with divinyl benzene utilizing an initiator, i.e., persulfate/bisulfite, which is not a chain transfer agent. The ratio of styrene to butylacrylate was 77:23, and about 0.24 weight percent of a 55 weight percent divinyl benzene solution and about 1 to 2 weight percents of the catalyst were utilized. The weight percent of the divinyl benzene and catalyst utilized are based upon the total weight of the toner composition.

A toner powder was made by compounding 30.0 g of the toner composition and 1.80 g of Regal 300 in an 8" roll mill for a time period of 20 minutes at a temperature of 130° C.

The charge/mass measurement was 7.6 μcoul/g which is too low of a charge level to provide stable developer performance.

The fusing temperature was 375° F.

EXAMPLE 4

Toner Composition Combined With 2-Phenyl-2-Imidazoline

A toner powder was prepared from 0.25 g of 2-phenyl-2-imidazoline, 32.0 g of the toner composition of Example 2 and 1.80 g of Regal 300 using the compounding process of Example 3.

The charge/mass measurement was 36.4 μcoul/g which is a good charge for developer performance.

The fusing temperature remained at 375° F.

EXAMPLE 5

Comparative Toner Powder Utilizing A Quaternary Ammonium Compound

A toner powder was prepared from 0.30 g of the N-octadecyl-N,N-dimethylbenzylammonium m-nitrobenzenesulfonate, 30.0 g of the toner composition of Example 2 and 1.80 g Regal 300 using the compounding process of Example 3.

The charge/mass measurement was 16.2 μcoul/g which is a good charge for developer performance.

The fusing temperature was greater than 425° F., the highest temperature attainable with the fuser, and did not achieve a "fair" rating. Therefore, this toner powder did not exhibit adequate fusing.

EXAMPLE 6

Styrene/Butyl Acrylate Toner Composition Combined With 2-Phenyl-2-Imidazoline

A toner composition was prepared by suspension polymerizing styrene butylacrylate (80/20) and the crosslinker divinyl benzene 1.3 weight percent of a 55 percent divinyl benzene solution. In addition to an initiator, i.e., 2,2'-azobis(2-methylbutane nitrile), the chain transfer agent t-dodecanethiol (1.9 wt. %) was also utilized to control the molecular weight of the toner binder.

A toner powder was prepared from 0.25 g of 2-phenyl-2-imidazoline, 32.0 g of the toner composition and 1.80 g of Regal 300 using the compounding process of Example 3.

The charge/mass ratio was 47.5 μcoul/g which is rather high for a toner to give good developer performance. However, this high charge/mass measurement could be compensated for by the proper choice of carrier.

The onset of fusing temperature was 340° F. which is very good.

EXAMPLE 7

Toner Composition Combined With 2-Phenyl-2-Imidazoline

A toner composition was prepared by suspension polymerizing styrene, butyl acrylate and the crosslinker divinyl benzene utilizing an initiator, i.e., 2,2'-azobis(2-methylbutane nitrile), that is not a chain transfer agent. The weight ratio of styrene to butyl acrylate was 77:23 and 0.32 weight percent of a 55 percent solution of divinyl benzene and about 1 to 2 weight percent of the catalyst were utilized, based on the total weight of the toner composition.

A toner powder was prepared from 0.25 g of 2-phenyl-2-imidazoline, 32.0 g of the toner composition, and 1.80 g of Regal 300 using the process of Example 3.

The charge/mass ratio was 38.7 μcoul/g which is a good charge for developer performance.

The onset of fuser temperature was 375° F. which is good.

EXAMPLE 8

Toner Powder Containing 2-Phenyl-2-Imidazoline

A toner composition was prepared from 0.60 g of 2-phenyl-2-imidazoline, 60.0 g of Cargill 3018, 1.86 g of ECN 1273 and 3.67 g of Regal 300 using the process of Example 2.

The charge/mass measurement was 31.5 μcoul/g which is a good charge for developer performance.

The onset of fusing temperature was 310° F. which is very good.

EXAMPLE 9

Toner Powder Containing 2-(2-Hydroxyphenyl)-2-Imidazoline

A toner composition was prepared from 0.60 g of the charge control agent 2-(2-hydroxyphenyl)-2-imidazoline, 60.0 g of Cargill 3018, 1.86 g of ECN 1273 and 3.67 g of Regal 300 using the process of Example 2.

The charge/mass measurement was 35.1 μcoul/g which is a good charge for developer performance.

The onset of fusing temperature was 300° F. which is very good.

EXAMPLE 10

Toner Powder Containing 2-(4-Methylphenyl)-2-Imidazoline

A toner powder was prepared from 0.60 g of the charge control agent 2-(4-methylphenyl)-2-imidazoline, 60.0 g of Cargill 3018, 1.86 g of ECN 1273 and 3.67 g of Regal 300 using the process of Example 2.

The charge/mass measurement was 32.1 μcoul/g which is a good charge for developer performance.

The onset of fusing temperature was 315° F. which is very good.

EXAMPLE 11

Toner Powder Containing 2-(2-Chlorophenyl)-2-Imidazoline

A toner powder was prepared from 0.60 g of the charge control agent 2-(2-chlorophenyl)-2-imidazoline, 60.0 g of Cargill 3018, 1.86 g of ECN 1273 and 3.67 g of Regal 300 using the process of Example 2.

The charge/mass measurement was 44.6 μcoul/g which, although it is high, is a good charge for developer performance.

The onset of fusing temperature was 300° F. which is very good.

Example 12

Toner Powder Containing 2-(4-Chlorophenyl)-2-Imidazoline

A toner powder was prepared from 0.60 g of the charge control agent 2-(4-chlorophenyl)-2-imidazoline, 60.0 g of Cargill 3018, 1.86 g of ECN 1273 and 3.67 g of Regal 300 using the process of Example 2.

The charge/mass measurement was 23.9 μcoul/g which is a good charge for developer performance.

The onset of fusing temperature was 315° F. which is very good.

We claim:

1. A toner composition comprising:
   about 75 to about 98 weight percent of a binder selected from the group consisting of a polyester having a number average molecular weight in the range of about 1,000 to about 4,000 that is cross-linked with a multifunctional epoxy novolac resin and a styrene/butyl acrylate copolymer; and
   a charge control agent selected from the group consisting of 2-phenyl-2-imidazoline, 2-(2-hydroxyphenyl)-2-imidazoline, 2-(2-chlorophenyl)-2-imidazoline, 2-(4-chlorophenyl)-2-imidazoline, 2-(4-methylphenyl)-2-imidazoline, 2-n-undecyl-2-imidazoline, 2-benzyl-2-imidazoline, 4,4-dimethyl-2-imidazoline, 1,5-diazabicyclo[4.3.0]non-5-ene, 2,8-diazabicylco[5.4.0]undec-7-ene, 1-methyl-2-phenylbenzimidazole and imidazo[1,2-a]pyridine.

* * * * *